(12) United States Patent
Axborn et al.

(10) Patent No.: US 11,617,692 B2
(45) Date of Patent: Apr. 4, 2023

(54) ABSORBENT ARTICLE INCLUDING A CONFORMANCE ZONE WHICH INCLUDES ABSORBENT CLUSTERS

(71) Applicant: Essity Hygiene and Health Aktiebolag, Gothenburg (SE)

(72) Inventors: Peter Axborn, Gothenburg (SE); Anders Östin, Gothenburg (SE); Helena Corneliusson, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 17/624,273

(22) PCT Filed: Jun. 30, 2020

(86) PCT No.: PCT/SE2020/050684
§ 371 (c)(1),
(2) Date: Dec. 31, 2021

(87) PCT Pub. No.: WO2021/015653
PCT Pub. Date: Jan. 28, 2021

(65) Prior Publication Data
US 2022/0313503 A1    Oct. 6, 2022

(30) Foreign Application Priority Data
Jul. 19, 2019  (WO) .................. PCT/SE2019/050705

(51) Int. Cl.
*A61F 13/532* (2006.01)
*A61F 13/535* (2006.01)

(52) U.S. Cl.
CPC .......... *A61F 13/532* (2013.01); *A61F 13/535* (2013.01)

(58) Field of Classification Search
CPC ............................. A61F 13/532; A61F 13/535
See application file for complete search history.

(56) References Cited

U.S. PATENT DOCUMENTS

| 4,055,180 A | 10/1977 | Karami |
| 5,977,430 A | 11/1999 | Roe et al. |

(Continued)

FOREIGN PATENT DOCUMENTS

| EP | 1000597 A2 | 5/2000 |
| EP | 2130522 A1 | 12/2009 |

(Continued)

OTHER PUBLICATIONS

International Preliminary Report on Patentability (Form PCT/IB/373) and the Written Opinion of the International Searching Authority (Form PCT/ISA/237) dated Jan. 25, 2022, by the International Bureau of WIPO, in corresponding International Application No. PCT/SE2020/050684. (6 pages).

(Continued)

*Primary Examiner* — Michele M Kidwell
(74) *Attorney, Agent, or Firm* — Buchanan Ingersoll & Rooney P.C.

(57) ABSTRACT

An absorbent article including an absorbent core sandwiched between a liquid-permeable topsheet and a liquid-impermeable backsheet. The absorbent article includes a front portion, a back portion and a crotch portion located between the front portion and the back portion, wherein the absorbent core includes a coherent area, the coherent area being disposed in at least the front portion and the crotch portion of the absorbent article. The back portion of the absorbent article includes a conformance zone, the conformance zone including a plurality of absorbent clusters.

20 Claims, 5 Drawing Sheets

(56) References Cited

U.S. PATENT DOCUMENTS

| | | | |
|---|---|---|---|
| 6,231,556 B1* | 5/2001 | Osborn, III | A61F 13/47272 |
| | | | 604/385.101 |
| 2010/0069868 A1* | 3/2010 | Noda | A61F 13/4704 |
| | | | 604/378 |
| 2010/0121296 A1* | 5/2010 | Noda | A61F 13/532 |
| | | | 604/378 |
| 2013/0226120 A1 | 8/2013 | Van | |
| 2015/0342796 A1 | 12/2015 | Bianchi et al. | |

FOREIGN PATENT DOCUMENTS

| | | |
|---|---|---|
| EP | 2679209 A1 | 1/2014 |
| EP | 2949299 A1 | 12/2015 |
| EP | 2949300 A1 | 12/2015 |
| EP | 2949302 A1 | 12/2015 |
| TW | M540622 U | 5/2017 |

OTHER PUBLICATIONS

International Search Report (PCT/ISA/210) and Written Opinion (PCT/ISA/237) dated Sep. 7, 2020, by the Swedish Patent Office as the International Searching Authority for International Application No. PCT/SE2020/050684. (14 pages).

\* cited by examiner

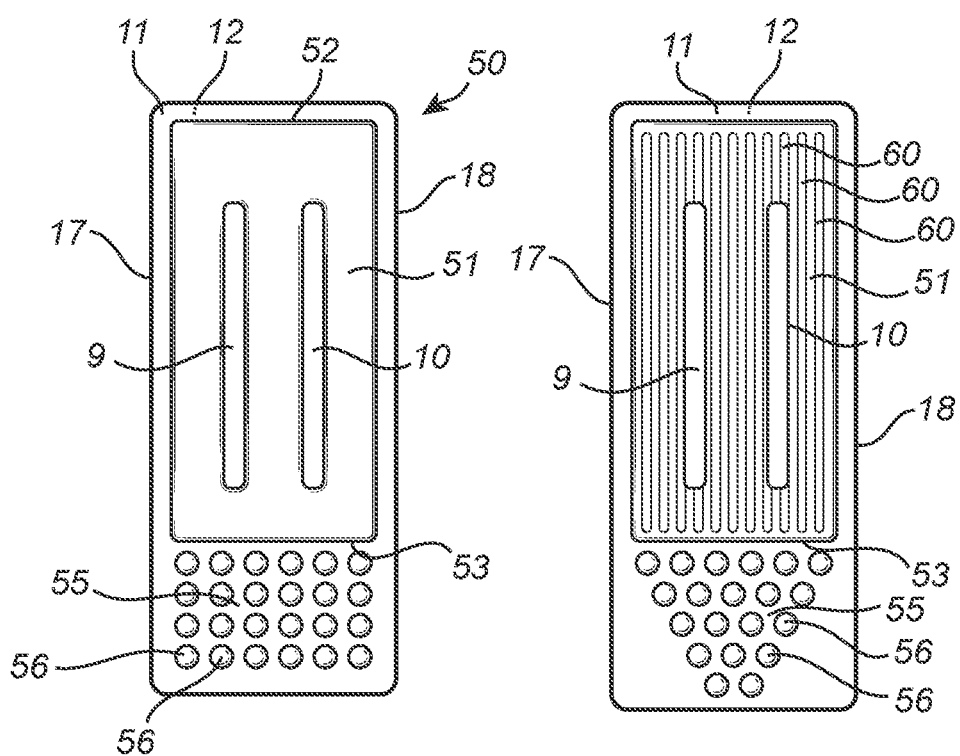

ABSORBENT ARTICLE INCLUDING A CONFORMANCE ZONE WHICH INCLUDES ABSORBENT CLUSTERS

TECHNICAL FIELD

The disclosure pertains to an absorbent article comprising an absorbent core which is sandwiched between a liquid-permeable topsheet and a liquid-impermeable backsheet. The absorbent core comprises an absorbent component which is enclosed by a core cover.

BACKGROUND

In the field of disposable absorbent articles, such as disposable absorbent diapers and pant-type articles, there is a general desire to provide the absorbent articles with a snug and body conforming fit as well as absorbency and leakage security. In addition, there is a continuing need for improvements in particular with regard to reduction of material consumption as well as cost efficiency when manufacturing disposable absorbent articles. There is also an increasing concern that the amount of material used in disposable absorbent articles is kept to a minimum from an environmental point of view. Hence, there is a desire for disposable absorbent articles which occupy less space during transporting, require less raw material, and are less voluminous when being disposed of without sacrificing functionality.

EP 2 949 302 A1 discloses an absorbent core which is substantially free of cellulose fibers and which consists of a plurality of discrete strips of absorbent material. The absorbent core has curved channel-forming areas formed in an absorbent core

SUMMARY

The present disclosure is based on the insight that an absorbent article having improved fit and body conformance as well as good functionality with regard to absorbency and leakage security, may be achieved by a combination of selected features in an absorbent core of the article.

The absorbent articles referred to herein are wearable and disposable absorbent articles, for example in the form of open diapers, pant diapers, belted diapers, incontinence garments, feminine hygiene garments and the like, as well as absorbent inserts which are worn inside a support garment, such as a support pant or ordinary underwear. The articles are used to absorb, distribute and store various types of body exudates while providing a high level of comfort and a sense of dryness to the wearer during use.

Disposable absorbent articles having good functionality, fit and body conformance may be achieved at least in part by the features of the disclosure.

Disclosed herein is an absorbent article comprising an absorbent core which is sandwiched between a liquid-permeable topsheet and a liquid-impermeable backsheet. The article has a longitudinal direction along a longitudinal axis and a transverse direction along a transverse axis, the transverse axis extending in a direction perpendicular to the longitudinal axis. The absorbent article has a front end edge and a back end edge extending in the transverse direction and a first side edge and a second side edge extending in the longitudinal direction. The absorbent article comprises a front portion, a back portion and a crotch portion located between the front portion and the back portion. The absorbent core comprises an absorbent component, the absorbent component being enclosed by a core cover comprising an upper side and a lower side, the absorbent component comprising a coherent area, the coherent area having an extension in said longitudinal direction in at least the front portion and the crotch portion of the article, and having an extension in the transverse direction over a full width of the absorbent component inside the core cover, the coherent area having a front edge and a back edge. The back portion of the absorbent article further comprises a conformance zone, the conformance zone comprising 2 to 200 absorbent clusters.

The front, back and crotch portion of the absorbent article may each form about a third of the length of the absorbent article. The absorbent core may be in the crotch portion and extend at least partially into the front and back portions of the absorbent article. The core may extend further into the front portion than the back portion of the absorbent article.

The core comprises an absorbent component being enclosed by a core cover, the core cover comprising an upper side and a lower side. Accordingly, an absorbent component is a part of the absorbent article which is enclosed in a core cover. The absorbent component may constitute all or part of the absorbent core, as set out herein.

The absorbent component which is enclosed by the core cover, may comprise both the coherent area of the absorbent core and the conformance zone or only the coherent area of the absorbent core. In the latter case, the conformance zone may be provided as a separate component which may or may not be enclosed by a core cover. When enclosed by a core cover, the upper and lower sides of the core cover may or may not be attached, such as by adhesive, in areas outside the absorbent clusters. An absorbent material composition may be the same in the coherent area and in the conformance zone.

In the coherent area of the absorbent component, the absorbent material is interconnected such that there are unbroken fluids distribution paths within the absorbent material in the longitudinal direction from the front edge of the coherent area to the back edge of the coherent area as well as in the transverse direction from one side edge of the coherent area to the opposite side edge of the coherent area. The coherent area extends at least in the front portion and the crotch portion of the absorbent article and extends in the transverse direction over the full width of the absorbent component inside the core cover. Thus, fluids which are absorbed by the absorbent material in the coherent area of the absorbent component can be distributed in the core component both in the longitudinal direction and in the transverse direction e.g., under the action of capillary forces within the absorbent material in the coherent area of the absorbent component. The coherent area may be framed by absorbent material such that any channel therein stops short from the front edge, the back edge, the first side edge and the second side edge of the coherent area.

As set out herein, the coherent area may comprise absorbent cellulose fibres, such as wood pulp fibers. The absorbent cellulose fibres form a capillary network promoting liquid distribution in the coherent area of the absorbent core.

The coherent area may be a primary absorption area of the absorbent article and is configured to provide a major part of the absorption capacity of the absorbent article. The coherent area together with the conformance zone ascertain that the liquid which reaches the absorbent article during use is safely absorbed, distributed and retained by the absorbent core. The coherent area may have any suitable shape, such as rectangular shape, hourglass shape, etc., as known in the art.

As disclosed herein, the absorbent clusters in the conformance zone may have a circular, oval or polygonal shape or a mixture of different shapes. The absorbent clusters may have the same size or may differ in size within the conformance zone.

The absorbent clusters may be fibre clusters comprising or consisting of absorbent cellulose fibres, such as wood pulp fibers. The absorbent cellulose fibres form a capillary network promoting liquid distribution.

The absorbent clusters may have indistinct or fuzzy peripheral edges and may even be interconnected by thinned edge portions of the clusters such that the absorbent clusters are perceived as being weakly connected with each other. Alternatively, the absorbent clusters may be completely separated by absorbent free channels between the absorbent clusters.

The arrangement of absorbent material in clusters separated by thinned areas or areas which are free or substantially free from absorbent material, makes the conformance zone soft and flexible and highly body conforming. The thinned or absorbent free areas offer less bending resistance than the thicker and stiffer material in the absorbent clusters.

In addition to providing a highly conformable back portion of the absorbent article, the arrangement of absorbent material in clusters saves material while still providing the absorbent article with appropriate absorbent capacity where needed. It has been found that by arranging the absorbent material in clusters, liquid which reaches the back portion of the article may be efficiently captured by a relatively small amount of absorbent material which is spread out in clusters over a part of the back portion of the absorbent article which may be reached by liquid during use of the absorbent article. By arranging the absorption material in clusters, the absorption material may provide adequate absorption capacity over a larger area than would have been possible with the same amount of absorbent material spread out in a uniform layer of material. Furthermore, when compared to a back portion having the same amount of absorbent material spread out in an even layer over the conformance zone the clusters serve to concentrate absorbed liquid to the clusters, thereby diminishing the wet area of the back portion. Accordingly, the conformance zone as disclosed herein offers efficient supplementary absorption of a relatively smaller amount of liquid which is not absorbed by the primary absorption material in the coherent area of the absorbent core.

Furthermore, the clustering of the absorbent material makes the back portion of the absorbent article airy due to the non-absorbent or less absorbent areas between the absorbent clusters, the non-absorbent or less absorbent areas which separate the absorbent clusters thus serving as air channels in the back portion of the absorbent article. There is also an advantageous cushioning effect of the absorbent clusters, reducing the contact surface between the absorbent article and the body of a wearer, in the rear portion of the absorbent article.

The conformance zone comprising the plurality of absorbent clusters may be non-contiguous with the coherent area. The conformance zone is considered to be non-contiguous with the coherent area if there is a distance between the back edge of the coherent area and a front edge of the conformance zone. A non-contiguous conformance zone may alternatively be described as being detached, separate or independent from the coherent area.

The conformance zone comprising the plurality of absorbent clusters may be contiguous with the coherent area, at least one of the absorbent clusters extending continuously in the longitudinal direction from the back edge of the coherent area. A contiguous absorbent cluster is an absorbent cluster which forms a continuation of the absorbent material in the coherent area of the absorbent core. The at least one contiguous absorbent cluster extends from the back edge of the coherent area towards the back end edge of the absorbent article.

The absorbent clusters in the plurality of absorbent clusters may be evenly or unevenly distributed in the transverse and/or in the longitudinal direction in the back portion of the core. Hence, the absorbent clusters may be arranged in a staggered pattern or in any other ordered or random pattern of evenly or unevenly distributed absorbent clusters. Furthermore, the absorbent clusters may be partly overlapping.

As disclosed herein, the conformance zone may comprise from 2 to 200 absorbent clusters, such as from 2 to 50 absorbent clusters, such as from 4 to 30 absorbent clusters.

The absorbent clusters in the plurality of absorbent clusters may be circular absorbent clusters having a diameter of from 2 to 45 mm, such as from 5 to 20 mm.

The conformance zone may be symmetrically orientated in relation to the longitudinal axis such that the conformance zone is mirror symmetric about the central longitudinal axis through the absorbent article. The conformance zone may have a triangular shape, a D-shape, a W-shape or a rectangular shape, including a square shape. When triangular or D-shaped, the conformance zone has a shape which narrows in a direction towards the back end edge of the absorbent article such that a width of the conformance zone adjacent the back edge of the coherent area of the absorbent core is greater than a width of the conformance zone adjacent the back end edge of the absorbent article. The width of the conformance zone may diminish gradually by equally sized steps, as in a triangular conformance zone. The width of the conformance zone may be constant in a front area closest to the back edge of the coherent area and diminish only at the back end of the conformance zone, as in a D-shaped conformance zone. The width of the conformance zone may be constituted by two or more rectangular sub-zones of different width with a more forward sub-zone having a greater width than a more rearward sub-zone or may have any other shape with a smaller width at the back part of the conformance zone than at the front part of the conformance zone.

A triangular or D-shaped conformance zone has been found to be in agreement with spreading patterns observed in user tests, wherein means for liquid absorption has been shown to be primarily needed in a central longitudinal area of the back portion of the absorbent core, with less or no absorption capacity needed near the longitudinal sides of the back portion of the absorbent core.

The number of absorbent clusters in the transverse direction of the conformance zone may decrease gradually in a direction towards a back edge of the absorbent core. If the absorbent clusters are of equal size in the transverse direction and are equally spaced apart in the transverse direction of the article, the width of the conformance zone diminishes as the number of absorbent clusters arranged in the transverse direction decreases.

The absorbent clusters may be of the same or generally the same size as seen in a plane defined by the transverse axis and the longitudinal axis or may be of different sizes. The size of the absorbent clusters may diminish in a direction towards the back edge of the absorbent core and/or in a direction from the central longitudinal axis of the absorbent article towards the side edges of the absorbent article.

The plurality of absorbent clusters in the conformance zone may comprise rod shaped clusters. The rod shaped clusters may be arranged parallel or generally parallel to each other in the longitudinal direction of the absorbent article. The rod shaped clusters may be distributed in the transverse direction over a triangular area of the absorbent article, the triangular area having its base arranged at the back edge of the coherent area and its tip arranged on the central longitudinal axis of the absorbent article and facing the back edge of the absorbent core. There may be 2-20 rod shaped clusters, such as 3-10, in the conformance zone.

The back edge of the coherent area may be non-linear and may have at least one aberration, such as one or more protrusions extending away from a straight base line or a baseline having an even curvature. The back edge of the coherent area may have the form of a baseline from which evenly distributed protrusions extend in a direction toward the back end edge of the absorbent article.

The protrusions of the back edge of the coherent area may be in the form of semi-circles extending longitudinally away from the front end edge of the absorbent article and towards the back end edge of the absorbent article.

The coherent area of the absorbent core may comprise oblong areas extending in the longitudinal direction from the front end edge of the absorbent article towards the back end edge of the absorbent article at least in a front portion of the coherent area. The oblong areas are regions of the absorbent core in which absorbent material has been accumulated. The oblong areas may have a greater thickness than the parts of the coherent area which are not occupied by the oblong areas. The oblong areas may have a higher basis weight than the parts of the coherent area which are not occupied by the oblong areas. The oblong areas may have a higher density than the parts of the coherent area which are not occupied by the oblong areas. The oblong areas may have any combination of greater thickness, higher basis weight and higher density than the parts of the coherent area which are not occupied by the oblong areas.

The oblong areas may extend in the longitudinal direction of the absorbent article, all the way or substantially all the way from the front edge to the back edge of the coherent area.

A density of absorbent material may be higher in the oblong areas than in the clusters in the conformance zone in the back portion of the absorbent article. The absorbent material in the oblong areas may have a greater thickness than the absorbent clusters in the conformance zone in the back portion of the absorbent article. The absorbent material in the oblong areas may have a higher basis weight than the absorbent clusters in the conformance zone in the back portion of the absorbent article.

A number of oblong areas extending in the longitudinal direction of the absorbent article may be from 3 to 20 oblong areas, such as from 4 to 15 oblong areas or from 5 to 10 oblong areas.

The density of absorbent material in said oblong areas may be 10-90% higher, such as 20-70% higher, than in said plurality of absorbent clusters in said conformance zone in said back portion of said absorbent article.

The density of absorbent material in said stiffening segment in the crotch portion of said absorbent article may be 5-70% higher than in said oblong areas in the front portion of said absorbent article, such as 10-50% higher.

The density of the absorbent material in the oblong areas may be at least 130 kg/m$^3$ and below 300 kg/m$^3$, such as at least 150 and below 200 kg/m$^3$.

The oblong areas may have a width of 3-30 mm, such as 5-20 mm.

The absorbent component may comprise oblong areas of absorbent material extending in said longitudinal direction at least in the front portion and the crotch portion of said absorbent article. The oblong areas may extend in said longitudinal direction substantially from said front edge to said back edge of said coherent area.

The oblong areas may be delimited in the transverse direction by low density areas of absorbent material. The low density areas may have a width of less than 5 mm and more than 0.5 mm. The density of the absorbent material in the low density areas may be less than 50 kg/m$^3$.

A modified circular bend stiffness may be at least 50% higher in the front portion of the absorbent article comprising oblong areas than in said conformance zone in the back portion of the absorbent article.

As disclosed herein, an absorbent component, including the coherent area, may be enclosed in a core cover. The coherent area of the absorbent component may comprise one or more sealed channels extending in the longitudinal direction in the crotch portion of the absorbent article, such as a first sealed channel and a second sealed channel, the sealed channels having seals extending therein, the seals joining the upper and lower sides of the core cover within the sealed channels. The sealed channels may be permanent channels, implying that the seals joining the upper and lower sides of the core cover remain unbroken during normal use of the absorbent article. Furthermore, the seals in the sealed channels restrain the cover material and prevent the absorbent material in the absorbent component from expanding into and closing the sealed channels upon wetting of the absorbent component. The channels may be free from absorbent material.

The absorbent article may further comprise two side seams being arranged along longitudinal side edges of the absorbent component. In a coherent area having two sealed channels, a center segment having a first width is defined in the absorbent component between the sealed channels, and two side segments each having a second width are defined in the absorbent component outside each channel seal between each channel seal and a corresponding one of the side seams.

The absorbent component in the crotch portion may be configured so that 33-41 weight % of the absorbent material is in the center segment and 25-33 weight % of the absorbent material is in each one of the side segments.

When defining that the total amount of absorbent material in a center segment located between two sealed channels is generally equal to, or greater than the total amount of absorbent material in each one of the side segments, is meant that the total weight of the absorbent material in the center segment is generally equal to, or greater than, the total weight of the absorbent material in each one of the side segments.

The provision of sealed channels in the absorbent component contributes to improving fit, comfort and function of the absorbent article in its wet condition. It is offered an absorbent article in which the crotch portion, and in particular a segment between two sealed channels, may be configured to develop an increased stiffness as compared with the remaining parts of the absorbent core. There is a well-known problem with sagging in the crotch portion of an absorbent article as the article absorbs liquid which accumulates in the crotch portion. The sagging problem will gradually increase as the amount of liquid absorbed by the article increases. An absorbent article, as disclosed herein and being provided with at least two sealed channels, is constructed so that the stiffness in the segment of the absorbent component which is located between the sealed channels increases gradually with the amount of liquid absorbed by the article. Initially, when only a small amount of liquid has been absorbed, the problem with sagging is negligible, and therefore the stiffness in the center segment does not need to be high. As the amount of absorbed liquid increases, the problem with sagging increases proportionally, and so a higher stiffness in the center segment is desirable to counteract the weight of the absorbed liquid in the crotch portion.

Furthermore, according to the present disclosure, absorbent side segments arranged between side seams of the absorbent component and sealed channels will not, at least not to any substantial extent, increase its stiffness in wet condition. The absorbent side segments will ensure that the total absorbent capacity in the crotch portion is sufficient while remaining relatively soft and pliable, as compared to the stiffened portion or portions located between sealed channels. According to the present disclosure, an absorbent article is obtained having a reduced tendency for sagging while at the same time having sufficient absorption capacity in the crotch portion and also being comfortable to wear for the user.

The core cover enclosing a stiffening segment located between two sealed channels thus defines and limits the expansion space for the absorbent material in the stiffening segment. In the absorbent articles as disclosed herein, it is not necessary that the expansion space is completely closed around the stiffening segment or segments between the sealed channels, only that the swelling of the absorbent material in the stiffening segment or segments is restricted, at least in the transverse direction of the absorbent article. The ends of a stiffening segment may be open such that fluid may pass in the longitudinal direction out of the stiffening segment.

The absorbent article may comprise leg elastic elements extending along all or a part of each longitudinal side edge of the absorbent article. If one or more longitudinally extending channel is provided in the crotch portion of the absorbent article, the leg elastic elements may have a greater length in the longitudinal direction of the absorbent article than the length of the one or more longitudinally extending channel.

The leg elastic elements may extend in the longitudinal direction of the article in the crotch portion of the absorbent article and in part of the front portion and/or part of the back portion of the absorbent article. The leg elastic elements may have a greater extension in the back portion than in the front portion.

The leg elastic elements may cooperate with features of the absorbent component such as the oblong areas and sealed channels as disclosed herein to promote shaping and fit of the absorbent article during use.

A ratio of a width of a center segment of the absorbent component as measured in the transverse direction between two sealed channels and a distance in the transverse direction between the leg elastic elements may be from 0.10 to 0.30, from 0.15 to 0.25 or from 0.18 to 0.22.

The article may comprise a waist elastic feature located in the back portion at the back end edge of the absorbent article. A waist elastic feature, together with the leg elastic elements and the absorbent component comprising a stiffening segment located between two sealed channels and two side segments according to the present disclosure contribute to an improved fit of the article during use. In addition to or instead of a waist elastic feature in the back portion of the absorbent article, a waist elastic feature may be located in the front portion of the absorbent article. Waist elastic features may extend only partly along the front and/or the back end edge or may extend the full length of the front and/or the back end edge, i.e. from the first side edge to the second side edge of the absorbent article.

A core cover as disclosed herein may be formed by a separate upper core cover layer forming the upper side of the core cover and a separate lower core cover layer forming the lower side of the core cover, the upper and lower core cover layers together enclosing the absorbent component. A sealing arrangement may be provided for joining the upper and lower sides of the core cover. The disclosure is not limited to core covers comprising two separate core cover layers. The core cover may be formed from a single material layer. In such case the absorbent component may be enclosed by one core cover layer which is wrapped around the absorbent component or which is formed as a tubular structure into which the absorbent component is inserted. Furthermore, the core cover may be made from more than two core cover layers. The core cover may be sealed only in the longitudinal direction of the absorbent article, leaving the core cover open in both a front end of the core cover and in a back end of the core cover. Alternatively, the core cover may be sealed at one or both of the front end and the back end of the core cover. In the latter case, the absorbent component is completely enclosed inside the core cover.

The basis weight of the core cover material may be in the range of from 5 $g/m^2$ to 20 $g/m^2$. The core cover material may be made of thermoplastic polymer material, such as polyolefin, polyesters, polyamide and combinations thereof. The core cover material may be nonwoven material. The nonwoven material may be made of thermoplastic polymer material fibers or filaments. The nonwoven layer may be formed by any of a variety of different processes, such as spunbonding, airlaying, meltblowing or bonded carded web formation processes. The nonwoven layer may be made of co-formed lamina of nonwoven materials such as an SMS (spunbond/meltblown/spunbond) nonwoven material or an SS (spunbond/spunbond) nonwoven material. The thermoplastic polymer materials in the nonwoven layer may be polypropylene or bicomponent fibers of polypropylene and polyethylene, or of a combination of such materials.

An absorbent component as disclosed herein may be constituted by one single absorbent component layer which is wrapped in a core cover having an upper side and lower side.

Absorbent components comprising two or more layers are also contemplated for the absorbent cores as disclosed herein.

The absorbent component may have a rectangular shape. A rectangular absorbent component may have the advantage of being easy to manufacture and enclose by a core cover. The absorbent article may comprise a single core layer.

One or more channel may be arranged in the absorbent component such as one to five channels. The channel or channels may be arranged in the longitudinal direction of the absorbent article. The channel or channels may be free from absorbent material and the upper and lower sides of the core cover may be joined to each other by one or more channel seals being arranged in the channel or channels to form sealed channels. If two or more sealed channels are present in the coherent area, stiffening segments are formed between each two adjacent sealed channels.

The absorbent component may comprise a mixture of absorbent cellulose fibers, such as cellulose pulp fibers and superabsorbent polymer material in the form of particles, granules, fibers, flakes, etc. The absorbent material in the absorbent component, at least in the crotch portion, may be constituted by 50-100 weight % superabsorbent material and 0-50 weight % pulp material, or 70-100 weight % superabsorbent material and 0-30% pulp material.

The composition of the absorbent material may be the same in the coherent area and in the conformance zone. Hence, a mixture of superabsorbent material and pulp material may be the same in the coherent area and in the conformance zone.

The total absorbent capacity per cubic centimeter of the coherent area of the absorbent component in dry condition may be at least 15 $g/cm^3$, or at least 25 $g/cm^3$ or at least 35 $g/cm^3$.

The pulp material in the coherent area of the absorbent component may have a basis weight which is in the interval of 50-400 $g/m^2$ and the superabsorbent material may have a basis weight which is in the interval of 100-900 $g/m^2$.

The thickness of the coherent area of the absorbent component in dry condition, measured with an applied pressure of 0.5 kPa, may be in the range of from 1.0 to 5.5 mm or from 2.0 to 4.5 mm. A representative mean value may be obtained by measuring on several parts of the absorbent component.

The absorbent component may be formed using an air forming process, such as an air forming process carried out on an air forming drum, also referred to as a vacuum forming drum. The air forming drum operates by application of internal suction in the forming drum to draw flows of air suspended absorbent material into forming molds arranged on the surface of the forming drum.

The forming drum may have several forming molds arranged on the outer surface into which the absorbent material is deposited for continuously forming absorbent components. The shape and size of the forming molds determine the shape and size of the absorbent components. Each forming mold has a foraminous air permeable bottom on which the air suspended absorbent material is collected and accumulated as the air is drawn off into the interior of the forming drum. The amount of material deposited in different parts of the mold may be controlled by controlling the air flow through the foraminous bottom. To this end, the foraminous bottom of the mold may have different air permeability in different portions of the mold which may be accomplished by arranging masking plates in different parts of the mold and/or by shaping the foraminous bottom to create a mold with varying depth, corresponding to an absorbent component having different thickness in different parts. A first part of the mold may be arranged to produce the coherent area of the absorbent component as set out herein. The bottom of the first part of the mold may then comprise grooves corresponding to where oblong areas of accumulated material are to be formed which will form oblong high density areas in the coherent area of the absorbent component and/or one or more blocked areas where channels are to be formed in the absorbent component. A second part of the mold may be arranged to produce the conformance zone and may have a blocking plate having openings arranged therein, the openings being arranged in locations where the absorbent clusters are to be formed and having a shape and size corresponding to the shape and size of the absorbent clusters. The presence of blocking plates in the second part of the mold also serves to decrease the air permeability in this area of the mold, which causes a greater part of the air flow and concomitantly a greater part of the air suspended absorbent material to be drawn towards and collected in the first part of the forming mold.

The disclosure may be varied within the disclosed scope. For example, the materials and dimensions used for the different layers forming an absorbent article as disclosed herein may be varied, as indicated above. The absorbent article may further include any useful component or feature as known in the art such as fluid acquisition and distribution components, leg elastics, standing gathers, crotch and waist elastics, side panels, fastening systems, wetness indicators, skin care agents, disposal means, etc., as known in the art and depending of the type of absorbent article intended.

BRIEF DESCRIPTION OF THE DRAWINGS

The absorbent articles as disclosed herein will be further explained hereinafter with reference to the appended drawings wherein:

FIGS. 2A-2I show different core configurations;

DETAILED DESCRIPTION

Different aspects of the present disclosure will be described more fully hereinafter with reference to the enclosed drawings. The embodiments disclosed herein can, however, be realized in many different forms and should not be construed as being limited to the aspects set forth herein.

It is to be understood that the drawings are schematic and that individual components, such as layers of material are not necessarily drawn to scale.

Figure 1:
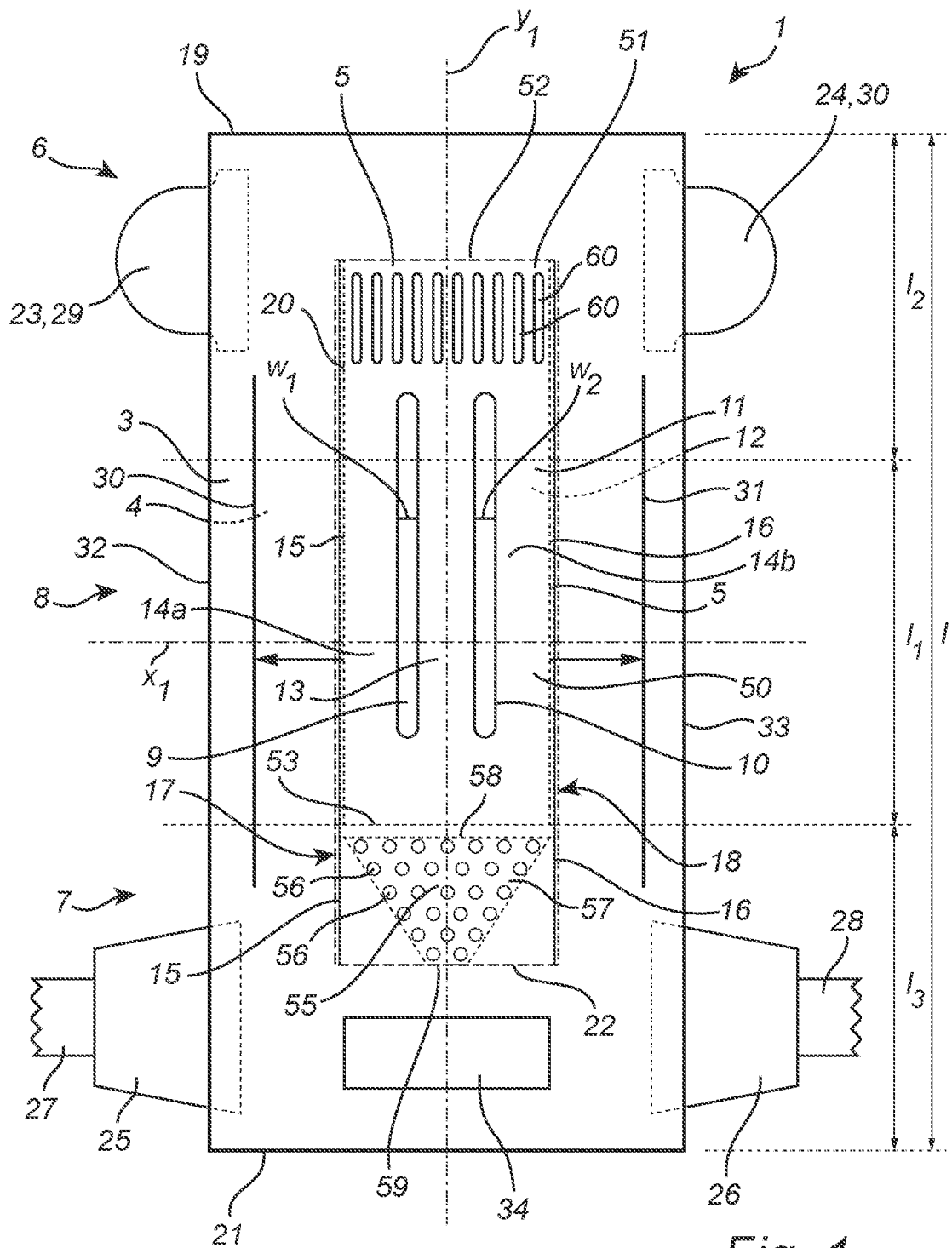
FIG. 1 shows a view from above of an absorbent article in the form of a diaper.

With initial reference to FIG. 1, there is shown an absorbent article 1 in the form of a baby diaper. The absorbent article 1 is shown in FIG. 1 in an unfolded and flat state with all elastic elements in an extended state.

The absorbent article 1 is seen from the surface which will be facing a wearer's body when the article is being worn and comprises a liquid-permeable topsheet 3, a liquid-impermeable backsheet 4 and an absorbent core 5 which is sandwiched between the topsheet 3 and the backsheet 4. The topsheet 3 is arranged at the inner or wearer-facing surface of the absorbent article 1, whereas the backsheet 4 is arranged at the outer or garment-facing surface of the absorbent article 1. Furthermore, as illustrated in FIG. 1, both the topsheet 3 and the backsheet 4 may extend laterally outside of the absorbent core 5 along the entire perimeter of the absorbent article 1. Alternatively, the topsheet 3 and the backsheet 4 may be generally coextensive with the absorbent core 5 or only one of the topsheet 3 and the backsheet 4 may extend outside the perimeter of the absorbent core 5. It is also conceivable that the topsheet 3 and the backsheet 4 extend outside of the absorbent core only along parts of the perimeter of the absorbent article, such as only along the side edges or only along one or both end edges or along the side edges and only one of the end edges.

The absorbent core shown in FIG. 1 has a rectangular design. However, as set out herein, the disclosure is not limited to this design and it is to be understood that the absorbent core may have any useful shape within the scope of the disclosure.

The topsheet 3, backsheet 4 and the absorbent core 5 may consist of any materials suitable for their purposes, as will be discussed in further detail below.

As shown in FIG. 1, the absorbent article 1 has a longitudinal direction along a central longitudinal axis y1 and a transverse direction along a central transverse axis x1, which is perpendicular to the longitudinal axis y1. Furthermore, the absorbent article 1 may be defined as being divided into a front portion 6 having a length $l_2$, a back portion 7 having a length $l_3$ and a crotch portion 8 having a length $l_1$. The front portion 6 has a front waist edge constituting a front end edge 19 of the absorbent article 1 and the back portion 7 has a back waist edge constituting a back end edge 21 of the absorbent article 1. Leg edges are formed by longitudinally extending side edges 32,33 of the absorbent article 1. The front portion 6 is the part of the absorbent article which is intended to be oriented in a direction towards the belly of the wearer during use of the absorbent article 1 and the back portion 7 is the part of the absorbent article which is intended to be oriented in a direction towards the buttocks of the wearer.

The absorbent article 1 in FIG. 1 is an open-type diaper having front fastener tabs 23, 24 extending from the side edges 32, 33 at the front end edge 19 of the absorbent article 1 and back fastener tabs 25, 26 extending from the side edges 32, 33 at the back end edge 21 of the absorbent article 1. When putting on the absorbent article 1 on a wearer, the back fastener tabs 25, 26 are brought forward towards the wearer's belly and are attached with fastener elements 27, 28, such as hook-type fastener elements onto mating fastener elements 29, 30, such as loop-type fastener elements which are provided on the front fastener tabs 23, 24. In the diaper shown in FIG. 1, the front fastener tabs are made of loop-type material, such that no separate fastener elements need to be provided. It is to be understood that male fasteners, such as hook-type fasteners may instead be placed at the front of the article while female fasteners may be placed at the back of the article. Furthermore, the fastening arrangement may differ from that shown in the Figs. and may be of any useful kind as known in the art. Accordingly, fastener belts, girdles, adhesive fastening systems, etc., may be used. It should also be noted that the fastening system is optional to the absorbent article 1, as the article may be designed for use as an absorbent insert, worn inside a pair of supportive pants or ordinary underpants. Such articles may be provided with fastening adhesive arranged on the outer surface of the backsheet, to allow the article to be fastened inside the pants. Furthermore, the absorbent article may be a pant-type article which is provided in a pre-assembled configuration, with closed side seams. Such articles may nevertheless be provided with a fastening system, to allow the article to be opened and reclosed.

The absorbent core 5 comprises an absorbent component 50 which is sandwiched between an upper core cover side 11 and a lower core cover side 12. The core cover is a component of the absorbent article 1 which is provided in addition to the topsheet 3 and the backsheet 4. The absorbent component 50 has a front edge 52 and a back edge 22.

The absorbent component 50 comprises a coherent area 51 which is disposed forward in the absorbent article 1 with a forward part of the coherent area 51 being located in the front portion 6 and a rearward part of the coherent area 51 being located in the crotch portion 8 of the absorbent article 1 and optionally extending also into the back portion 7 of the absorbent article 1. The coherent area 51 has a front edge 52 and a back edge 53. As can be seen in FIG. 1, the width of the absorbent core 5 within the coherent area 51 is defined by the width of the coherent area 51. The back portion 7 of the absorbent article 1 comprises a conformance zone 55 which is placed behind the coherent area 51 as seen in a direction towards the back end edge 21 of the absorbent article.

The coherent area 51 of the absorbent core 5 comprises oblong high density areas 60 extending in the longitudinal direction within the material in the front portion of the coherent area 51 towards the back end edge 21 of the absorbent article 1. The oblong areas 60 are regions of the absorbent core 5 in which absorbent material has been accumulated such that longitudinally extending striations are formed in the material of the coherent area 51. The number of oblong areas in FIG. 1 is 11, but may be varied as disclosed herein. The density of the absorbent material in the oblong areas 60 may be at least 130 kg/m³ and below 300 kg/m³. The oblong areas 60 have a width of 3-30 mm, such as 5-20 mm. The oblong areas 60 is delimited in the transverse direction by low density areas of absorbent material. The low density areas may have a width of less than 5 mm and more than 0.5 mm. The density of the absorbent material in the low density areas may be less than 50 kg/m³.

The conformance zone comprises a plurality of absorbent clusters 56. The absorbent clusters 56 may have any suitable shape such as a circular, oval or polygonal shape. The absorbent clusters may all have the same size and shape or may differ in size or shape or may differ both in size and shape.

In FIG. 1, the plurality of absorbent clusters 56 are shown as a plurality of generally circular accumulations of absorbent material which are arranged in a staggered pattern over a triangular area 57 of the absorbent component 50. The number of absorbent clusters 56 in the transverse direction of the conformance zone 55 decreases gradually in a direction towards the back edge 22 of the absorbent component 50.

The conformance zone 55 as shown in FIG. 1 is non-contiguous with the coherent area 51 of the absorbent component 50 as the conformance zone 55 is arranged at a distance from the coherent area 51. The triangular area 57 in which the absorbent clusters 56 are arranged has its base 58 arranged at a distance from the back edge 53 of the coherent area 51 and its tip 59 arranged on the central longitudinal axis y1 of the absorbent article and facing the back end edge 21 of the absorbent article 1.

Alternatively, the conformance zone may be contiguous with the coherent area of the core component. Such configurations are disclosed in the non-limiting examples illustrated in FIGS. 2D, 2E, 2F and 2H which show at least one of the absorbent clusters extending continuously in the longitudinal direction from the back edge 53 of the coherent area 51.

In the absorbent article 1 as shown in FIG. 1, the conformance zone 55 is enclosed by the upper and lower sides of the core cover 11, 12 and forms part of the absorbent component 50. The planar shape and size of the absorbent component is defined by the planar shape and size of the core cover. As disclosed herein, the core cover may be formed by two separate sheets of material which are sealed at least along their longitudinally extending side edges and optionally also along one or both of the transversely extending end edges. Alternatively, the core cover may be formed by a bi-folded sheet of material which may be folded in the longitudinal direction and sealed at least along the side edges which are opposite to the fold.

As illustrated in the figures, the absorbent clusters 56 may be evenly distributed in the transverse and/or in the longitudinal direction of the absorbent article 1. FIGS. 1, 2A, 2B, 2E and 2G show conformance zones 55 having absorbent clusters 56 which are evenly distributed both in the transverse and in the longitudinal direction. FIGS. 2C, 2D, 2F and 2H show conformance zones 55 having absorbent clusters 56 which are evenly distributed in the transverse direction. In all of the absorbent components illustrated in the figures, the conformance zone 55 is symmetrically orientated in relation to the longitudinal axis of the absorbent component 50 and, thus, of the absorbent article 1.

The coherent area 51 of the absorbent component 50 which is shown in FIG. 1 comprises oblong areas 60 extending in the longitudinal direction in a front portion of the coherent area 51.

The density of absorbent material may be higher in the oblong areas 60 than in the plurality of absorbent clusters 56 in the conformance zone 55 in the back portion 7 of the absorbent article 1.

The absorbent component 50 which is shown in FIG. 1 is formed with two longitudinally extending and generally straight sealed channels 9,10 in which the upper core cover side 11 is joined to the lower core cover side 12 by seals extending along the sealed channels 9,10. The seals may be provided as bond lines consisting of bonding elements arranged in a bond pattern. A width of each bond line may be less than a width of the corresponding sealed channel 9, 10 in which the bond line is arranged. Thereby, a slack is formed in the core cover material between the edge of the bond line and the edge of the sealed channel in which the bond line is placed. Such slack may be provided to allow expansion room for the absorbent material arranged on either side of the bond lines. The slack may be smaller on the inner side of each sealed channel 9,10 which is facing towards the centre of the absorbent article, and larger on the outer side of each sealed channel 9,10 which is facing towards the side edges of the absorbent article 1.

As set out herein, the disclosure is not limited to a core wrap comprising two core cover layers. The core cover may be of one single material layer. The absorbent component may be enclosed by one core cover layer folded in two, or enclosed by a continuous core cover sheet, thereby providing upper and lower core cover sides for wrapping the absorbent component.

The upper core cover side 11 and the lower core cover side 12 may be attached to each other by any useful means as known in the art, for example, by thermo-mechanical bonding, such as thermo-sealing, ultrasonic bonding, an adhesive or adhesives, stitching or the like, or combinations of the same.

The sealed channels 9,10 constitute sections of the absorbent component 50 which are free from absorbent material. Absorbent free channels may be obtained by manufacturing the absorbent component 50 using a mat forming process during which absorbent material is omitted from the areas which correspond to the sealed channels 9,10. In this manner, no absorbent material will be present in the sealed channels 9,10. The presence of absorbent material in the sealed channels 9,10 may negatively influence the strength of the seals between the upper and lower core cover sides 11, 12 and should be avoided.

As shown in FIG. 1, the absorbent component 50 may be divided into a stiffening segment 13 located centrally in the crotch portion 8 between the sealed channels 9,10 and two side segments 14a, 14b in the crotch portion 8. The sealed channels 9,10 are consequently configured so that they separate the three segments 13, 14a, 14b from each other in the crotch area 8.

The absorbent component 50 may be generally rectangular and may comprise two generally straight sealed channels 9, 10 which extend generally parallel to the longitudinal axis y1. The seals joining the upper and lower core cover sides 11, 12 have a corresponding first channel sealing width w1 and a second channel sealing width w2. The disclosure is not limited to a rectangular absorbent component 50 and generally straight sealed channels 9, 10, i.e. other geometrical configurations may be used.

Furthermore, the stiffening segment 13 is defined in the absorbent component 50 between the sealed channels 9, 10. The two side segments 14a, 14b are defined in the absorbent component 50 outside each sealed channel 9, 10. More precisely, the first side segment 14a is positioned between the first sealed channel 9 and a first side seam 15, whereas the second side segment 14b is positioned between the second sealed channel 10 and a second side seam 16. The side seams 15, 16 are configured for joining the upper core cover side 11 to the lower core cover side 12, suitably by means of ultrasonic welding or other relevant technologies as described above with reference to the seals joining the upper cover side 11 and the lower cover side 12 in the sealed channels 9, 10. Furthermore, the side seams 15, 16 extend along each side of the absorbent component 50, inward of and along a first side edge 17 and a second side edge 18 of the absorbent component 50.

As mentioned, the length l1 of the crotch portion 8 may be equal to the length of the sealed channels 9, 10, i.e. the sealed channels 9, 10 may be arranged only in the crotch portion 8. However, the side seams 15, 16 may not just be positioned along the crotch portion 8 but may also extend into the front portion 6 and/or the back portion 7 as set out in more detail below.

The absorbent article 1 in FIG. 1 also has leg elastic elements 30,31 extending along each longitudinal side edge 32,33 of the absorbent article 1. The leg elastic elements 30,31 have a greater length in the longitudinal direction than the length of the sealed channels 9, 10 in the longitudinal direction. Accordingly, the leg elastic elements have an extension not only in the crotch portion 8 but also in a part of the front portion 6 and the back portion 7. The leg elastic elements 30, 31 have a greater extension in the back portion 7 than in the front portion 6, as seen in FIG. 1.

The absorbent article 1 also has a waist elastic element 34 located in the back portion 7 close to the back end edge 21 of the absorbent article 1. It is to be understood that also the front end edge 19 may be provided with waist elastic, if desired.

The leg elastic elements and the waist elastic element are optional features of an absorbent article as disclosed herein.

As disclosed herein, the absorbent component 50 is formed with a sealing arrangement which is constituted by the two sealed channels 9, 10 and the two side seams 15, 16. The sealing arrangement is configured so that, in the crotch portion 8, the absorbent component 50 is divided into a centrally arranged stiffening segment 13 and two side segments 14a, 14b.

As disclosed herein, the absorbent material may comprise a mixture of cellulose pulp material and superabsorbent material. The absorbent component 50 may be configured so that the total amount of absorbent material of the stiffening segment 13 between the sealed channels 9, 10 is generally equal to or greater than the amount of absorbent material in either one of the side segments 14a, 14b between each sealed channel 9, 10 and the corresponding side seam 15, 16. This means that the available space for expansion of the absorbent material in the stiffening segment 13, as the absorbent article 1 becomes wet as it absorbs liquid during use, is less than a corresponding available expansion space for each side segment 14a, 14b. This will lead to a situation in which the stiffening segment 13 will be stiffer than the side segments 14a, 14b when the absorbent article is in its wet condition. The stiffened central stiffening segment 13 counteracts the tendency of the wet article to sag and hang down in the crotch portion 8.

The expression "generally equal" as used above for describing the amount of absorbent material in the stiffening segment 13 as compared with the side segments 14a, 14b should be understood as allowing for slight variations in the amount of absorbent material in the order of approximately ±5% in any part of the crotch portion 8.

A width of the stiffening segment 13 may be defined between the sealed channels 9, 10 and a width of the absorbent component 50 may be defined between the first and second side edges 17, 18 of the absorbent component 50. The ratio of the width of the stiffening segment 13 and the width of the absorbent component 50 may be in the range of from 0.25 to 0.45.

As disclosed herein, various types of materials may be used for the absorbent article 1. The topsheet 3 which is arranged to face the wearer of the absorbent article 1 when the article is being worn may comprise or consist of a fluid permeable nonwoven fabric, film, mesh or foam. The topsheet may be made from thermoplastic material, such as thermoplastic synthetic fibers, film or netting. The topsheet 3 may be sufficiently liquid-permeable to allow discharged body fluids to penetrate through the thickness of the topsheet 3. Also, the topsheet 3 may suitably be manufactured from a material which is compliant and soft-feeling to the skin of the wearer. The topsheet 3 may consist of a single layer or may have a laminate structure comprising a plurality of layers, for example, two or more layers. The layers may be made of the same material, or some or all of the layers may be made of different materials.

The layer of the topsheet 3 or, for the case of a laminate structure, one, some, or all layers of the topsheet may be made of a single web of material or may have portions made of different materials, e.g., within different parts of the wearer-facing surface of the topsheet.

The layer of the topsheet 3 or, for the case of a laminate structure, one, some or all layers of the topsheet may be a nonwoven material, a perforated plastic film, a plastic or textile mesh, or a liquid permeable foam layer. The layer of the topsheet 3 or, for the case of a laminate structure, one, some or all of the layers of the topsheet may be, for example, a hydrophilic, non-apertured nonwoven web of fibers, such as natural fibers, e.g., cotton or pulp fibers, synthetic fibers, e.g., polyester or polypropylene fibers, or a combination of these fibers. The topsheet may have a basis weight in the range of 8-40 $g/m^2$. However, the disclosure is not limited to topsheets having this basis weight.

Furthermore, the backsheet 4 may be constituted by a liquid-impermeable layer such as a polymeric film, for example a film of polyethylene or polypropylene. The backsheet 4 may be breathable. The materials which may be used for the backsheet 4 include thin and flexible fluid impermeable plastic films, or fluid impermeable nonwoven materials, fluid impermeable foams and fluid impermeable laminates. The backsheet 4 may be formed by a single layer, but may alternatively be formed by a multi-layered structure, i.e. a laminate, wherein at least one layer is fluid impermeable. Furthermore, the backsheet 4 may be elastic in any direction. Furthermore, the backsheet 4 may have a laminate structure comprising a liquid barrier sheet and a nonwoven layer arranged on top of each other (not shown in detail in the drawings), wherein the nonwoven layer is arranged at an outer side away from the wearer of the absorbent article 1 when worn.

The nonwoven layer may be made of thermoplastic polymer material fibers or filaments. The nonwoven layer may be formed by any of a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials. The nonwoven layer may have a basis weight in the range of 5-40 $g/m^2$.

The liquid barrier sheet may be made of a plastic material, for example a thermoplastic film material, and/or a nonwoven material. For example, the liquid barrier sheet may be formed as a plastic layer, e.g., a thermoplastic layer, or a plastic film, e.g., a thermoplastic film. Forming the liquid barrier sheet of a plastic material, such as a thermoplastic film material, allows for a particularly good printability of the liquid barrier sheet. The liquid barrier sheet may also contain paper fibers. The liquid barrier sheet may be a liquid impermeable, breathable or non-breathable layer. The liquid barrier sheet may consist of a single layer or have a laminate structure with a plurality of layers, e.g., two or more layers, three or more layers, or four or more layers. The layers of the liquid barrier sheet may be laminated, bonded or attached to each other, for example, by thermo and/or mechanical bonding, such as thermo-sealing, ultrasonic bonding, such as ultrasonic welding, an adhesive or adhesives, stitching or the like. The liquid barrier sheet may be a breathable microporous film. The microporous film may be made of a material comprising at least two basic components, namely a thermoplastic elastomeric polyolefin polymer and a filler. These components and, in some embodiments, additional other components may be mixed together, heated and subsequently extruded into a mono-layer or multi-layer film using any one of various film-producing processes, such as cast embossed, chill and flat cast, and blown film processes.

Regarding the choice of materials for the various layers in the absorbent article, the materials may be chosen with consideration for the bonding processes used when forming seals in between components of the absorbent article, such the seals in the sealed channels and the side seams. For example, if ultrasonic welding is chosen for joining the upper and lower core cover sides, the materials for the core cover may be chosen such that they can form a secure bond during ultrasonic welding, e.g. by at least one of the upper and lower side of the core cover comprising or consisting of thermoplastic polymer material.

The absorbent core 5, includes the absorbent component 50 and may include further absorbent components such as components which provide liquid acquisition and liquid distribution. The absorbent core is disposed between the topsheet 3 and the backsheet 4 to absorb the liquid, such as urine or other bodily fluids, which has passed through the topsheet 3. The absorbent component 50 may be a single-layer structure or may be a layered structure, e.g., within the coherent area. The absorbent component 50 may comprise suitable amounts of superabsorbent material. Such superabsorbent material is well known in the field of absorbent articles, and is constituted by a water-swellable and water-insoluble material which is capable of absorbing large quantities of fluid upon formation of a hydrogel. The absorbent component may contain superabsorbent material in the form of fibers or particles of absorbent polymer material. For example, the superabsorbent material may be surface cross-linked, partially neutralized polyacrylates. The superabsorbent material, e.g., the superabsorbent fibers or particles, may be mixed with other absorbent or liquid uptake material or materials, such as cellulose fluff pulp, and/or arranged in pockets or layers in the absorbent component 50. The amount of superabsorbent material and pulp in the absorbent component 50 may be from 0 to 50 weight % pulp fibers and from 50 to 100 weight % superabsorbent material, or from 0 to 30 weight % pulp fibers and from 70 to 100 weight % superabsorbent material.

The absorbent component 50 may further comprise components for improving properties of the absorbent core 5, such as core integrity and strength. For example, the absorbent component 50 may comprise a binder or binders, such as binder fibers. Resilient fibers, chemically stiffened fibers, etc., may be present in the absorbent component to counteract wet-collapse of cellulosic fibers. Such fibers may also be useful in retaining a fluid transporting capillary network in the absorbent component so that absorbent fluid may be distributed in the absorbent component and be absorbed by superabsorbent material also in parts of the absorbent component outside the initial wetting area of the absorbent article.

The core cover 11,12 may be formed by a separate upper core cover 11 layer and a separate lower core cover 12 layer. However, the disclosure is not limited to a core cover comprising two separate core cover layers. The core cover 11,12 may also be made of one single material layer. The absorbent component 50 may be enclosed by one core cover 11,12 layer which is folded in two and sealed along the open edges, or may be enclosed by a continuous, tubular core cover sheet, thereby providing upper 11 and lower core cover 12 sides for wrapping the absorbent component 5*a*,5*b*, 5*c*. The basis weight of the core cover 11,12 material may be in the interval of from 5 g/m$^2$ to 20 g/m$^2$. The core cover 11,12 material may be made of thermoplastic polymer material. The core cover material may be nonwoven material. The nonwoven material may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials.

Furthermore, the various layers and components of the absorbent article 1 may be attached by means of adhesive material, as known in the art. Such adhesive is not shown in the drawings.

One or more additional layers may be provided in the absorbent article 1. For example, an acquisition layer may be arranged between the absorbent component 50 and the topsheet 3. Such an additional layer may for example be in the form of an airlaid layer, a spunlace layer, a high-loft fiber material, an open-cell or perforated foam or any other type of material layer or combination of layers which may be used in an absorbent article to act as a liquid handling layer providing functions such as liquid acquisition, liquid absorption and liquid distribution. A liquid acquisition layer is adapted to quickly receive and temporarily store discharged liquid before the liquid can be absorbed by the absorbent component. Such acquisition layer may be composed of for example airlaid nonwoven, spunlace nonwoven, high loft nonwoven or foam materials. An airlaid nonwoven may be produced wood pulp fluff fibers which are dispersed and suspended in a fast-moving air stream and condensed onto a moving screen by means of pressure and vacuum.

With reference again to FIG. 1, each sealed channel 9, 10 may have a length l1 which corresponds to the longitudinal extension of the crotch portion 8. Each one of the sealed channels 9, 10 may have a length l1 which is between 5-50%, such as 10-50%, such as 28-38%, of the total length l of the absorbent article 1. Furthermore, each channel sealing 9, 10 may have a length l1 which is between 10-60%, such as between 20-60%, such as between 30-50%, of the length of the absorbent component 50.

A further parameter is the positioning of the sealed channels 9, 10 in the longitudinal direction of the absorbent article 1.

The position of the sealed channels 9, 10 in the longitudinal direction of the absorbent article 1 may be chosen so that each channel 9, 10 terminate at a distance from the front end edge 19 of the article 1 which is between 15-40%, such as between 22-25%, of the total length l of the article 1.

Furthermore, the topsheet may comprise at least one additive material such as a skin care composition. The additive may be located on parts of the topsheet which are disposed along the longitudinal side edges 32, 33 of the absorbent article 1 and/or along the longitudinal side edges 17, 18 of the absorbent component 50. An advantage with such placement of the additive material, is that as the parts of the absorbent article 1 which are arranged along the side edges normally will be closer to the body of the wearer of the absorbent article 1 than a longitudinally central part of the absorbent article 1, the skin care benefits of the additive may be obtained without the additive interfering with fluid acquisition through the topsheet 3 in the central part of the absorbent article 1.

FIGS. 2A-2I illustrate absorbent components 50 having different combinations of features. The absorbent components 50 shown in the examples of FIGS. 2A-2I should not be considered to be limiting to the absorbent articles as disclosed herein, as it should be understood that one or more features of the coherent area 51 in any one of FIGS. 2A-2I can be freely combined with features of the conformance zone 55 in any other of FIGS. 2A-2I. Furthermore, it is to be understood that the absorbent component may have uniform composition, such as a uniform mixture of cellulose fluff pulp and superabsorbent material or may be composed of sub-layers having different composition. The absorbent component may have different composition in different zones of the area of the absorbent component or of the area of any sub-layer in the absorbent component.

The absorbent components 50 in FIGS. 2A-2I may be used in the absorbent article in FIG. 1 or in any other absorbent article as disclosed herein.

With reference to FIG. 2A, the coherent area 51 of the absorbent component 50 is a layer of absorbent material having uniform thickness. Two sealed channels 9, 10 are arranged in the coherent area 51, as disclosed herein. The sealed channels 9, 10 may optionally be supplemented by side seals as disclosed herein. The conformance zone 55 is a non-contiguous conformance zone 55 which is composed of circular absorbent clusters 56 arranged in a regular, evenly distributed pattern over a rectangular area of the absorbent component 50.

With reference to FIG. 2B, the coherent area 51 of the absorbent component 50 is a layer of absorbent material having oblong areas 60 arranged therein. The oblong areas 60 extend generally all the way from the front edge 52 of the coherent area 51 to the back edge 53 of the coherent area 51. Two sealed channels 9, 10 are arranged in the coherent area 51, as disclosed herein. The sealed channels 9, 10 may optionally be supplemented by side seals as disclosed herein. The conformance zone 55 is a non-contiguous conformance zone 55 which is composed of circular absorbent clusters 56 arranged in a regular, evenly distributed pattern over a triangular area of the absorbent component 50.

Figures 2C, 2D:
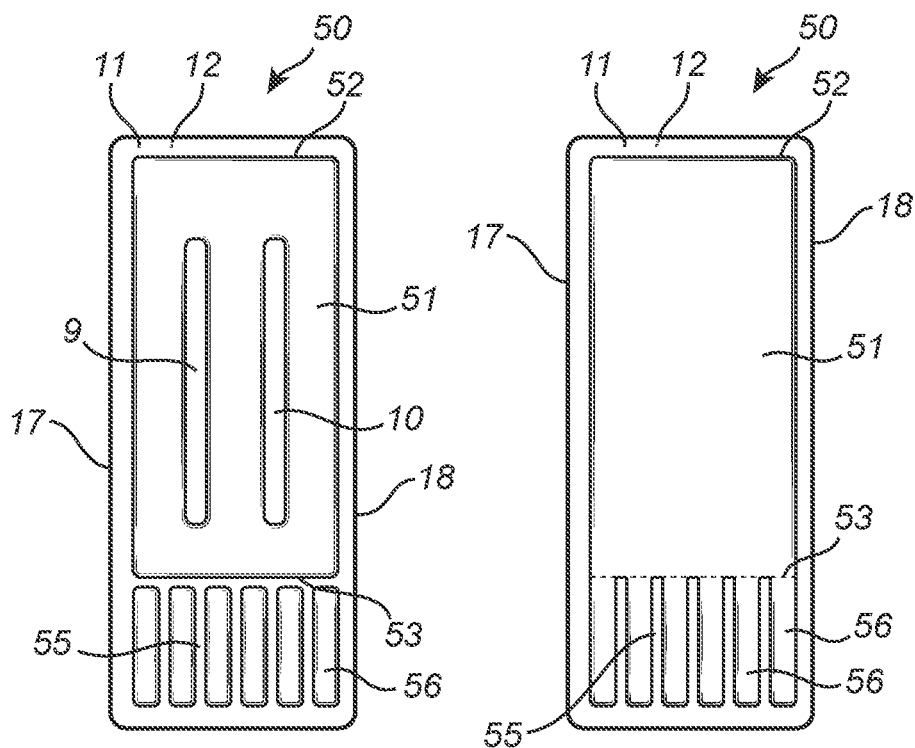

With reference to FIG. 2C, the coherent area 51 of the absorbent component 50 is a layer of absorbent material having uniform thickness. Two sealed channels 9, 10 are arranged in the coherent area 51, as disclosed herein. The sealed channels 9, 10 may optionally be supplemented by side seals as disclosed herein. The conformance zone 55 is a non-contiguous conformance zone 55 which is composed of rod-shaped absorbent clusters 56 arranged spaced apart in the transverse direction and in parallel to each other in the longitudinal direction over a rectangular area of the absorbent component 50.

With reference to FIG. 2D, the coherent area 51 of the absorbent component 50 is a layer of absorbent material having uniform thickness. The conformance zone 55 is a contiguous conformance zone 55 which is composed of rod-shaped absorbent clusters 56 arranged spaced apart in the transverse direction and in parallel to each other in the longitudinal direction over a rectangular area of the absorbent component 50. The rod-shaped absorbent clusters 56 extend in the longitudinal direction from the back edge 53 of the coherent area 51 and form continuations of the coherent area 51. Hence, the back edge 53 of the coherent area 51 constitutes a straight base-line from which the rod-shaped absorbent clusters 56 extend in a direction towards the back end edge (not shown in the figure) of the absorbent article.

Figures 2E, 2F:
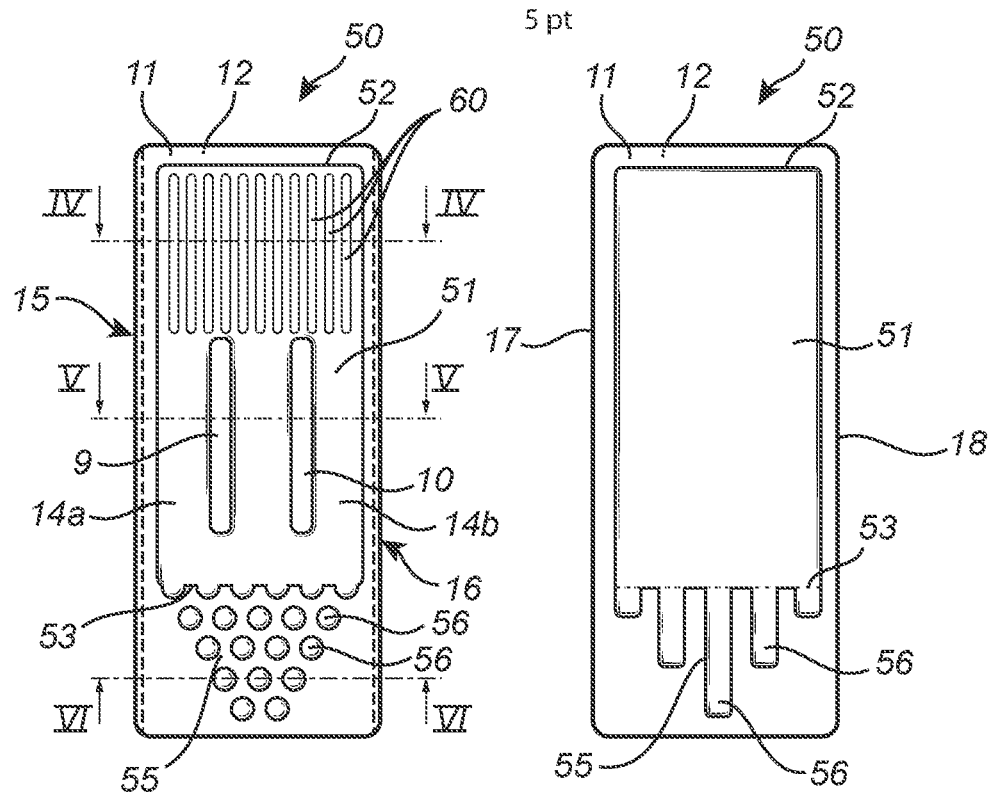

With reference to FIG. 2E, the coherent area 51 of the absorbent component 50 is a layer of absorbent material having oblong areas 60 arranged therein. The oblong areas 60 extend in the front portion of the coherent area 51, generally from the front edge 52 of the coherent area 51 to the front ends of two sealed channels 9, 10 which are arranged in the coherent area 51, as disclosed herein. The sealed channels 9, 10 may optionally be supplemented by side seals as disclosed herein. The conformance zone 55 is a contiguous conformance zone 55 which is composed of circular absorbent clusters 56 arranged in a regular, evenly distributed pattern over a triangular area of the absorbent component 50. The back edge 53 of the coherent area 51 is non-linear and may be seen as a straight baseline from which evenly distributed protrusions deviate in a direction towards the back end edge of the absorbent article. The protrusions on the back edge 53 of the coherent area 51 are in the form of semi-circles extending longitudinally away from the front end edge of the absorbent article 1 and towards the back end edge of the absorbent article. Hence, the protrusions may be seen as half absorbent clusters 56, which are continuous with the coherent area 51.

Figure 3:
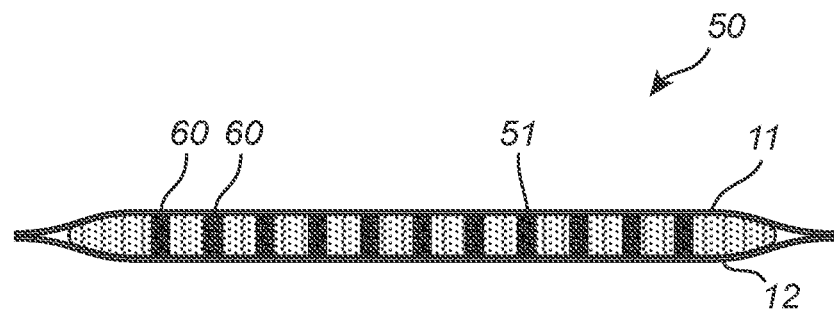
FIG. 3 shows a cross-section taken along the line IV-IV in FIG. 2E.

FIG. 3 shows a cross-section taken along the line IV-IV in the front portion of the absorbent component 50 shown in FIG. 2E. The oblong areas 60 are shown as thickened regions of the absorbent component 50. After formation of the absorbent component 50 in a forming mold, the absorbent component 50 will usually be compacted between two compaction rolls. As the amount of absorbent material is greater in the oblong areas 60, the density of the absorbent component 50 will generally be higher within the oblong areas 60 than in the areas of the absorbent component 50 located between and outside the oblong areas 60 unless measures are taken to avoid compaction of the material in the oblong areas 60.

Figure 4:
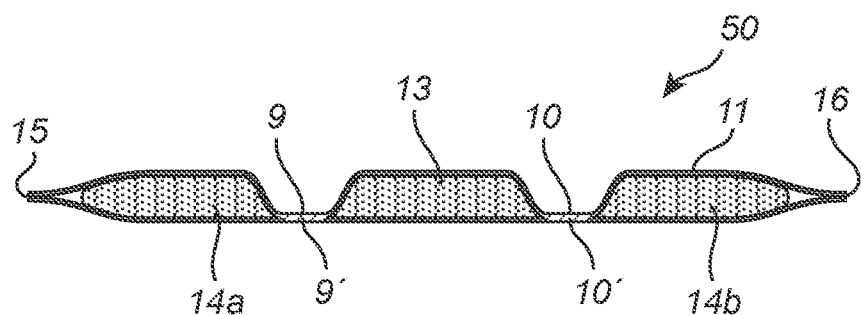
FIG. 4 shows a cross-section taken along the line V-V in FIG. 2E.

FIG. 4 shows a cross-section taken along the line V-V in the crotch portion of the absorbent component 50 shown in FIG. 2E. The absorbent component 50 which is shown has two longitudinally extending and generally straight sealed channels 9,10 in which the upper core cover side 11 is joined to the lower core cover side 12 by seals 9', 10' extending along the sealed channels 9,10, at the bottom of the sealed channels 9,10. The seals 9', 10' may be provided as bond lines consisting of bonding elements arranged in a bond pattern. A width of each bond line may be less than a width of the corresponding sealed channel 9, 10 in which the bond line is arranged. Thereby, a slack is formed in the core cover material between the edge of the bond line and the edge of the sealed channel in which the bond line is placed. Such slack may be provided to allow expansion room for the absorbent material arranged on either side of the bond lines. The slack may be smaller on the inner side of each sealed channel 9,10 which is facing towards the centre of the absorbent article, and larger on the outer side of each sealed channel 9,10 which is facing towards the side edges of the absorbent article 1.

Furthermore, a stiffening segment 13 is defined in the absorbent component 50 between the sealed channels 9, 10. Two side segments 14a, 14b are defined in the absorbent component 50 outside each sealed channel 9, 10, between the sealed channel 9,10 and a corresponding side seam 15, 16. Accordingly, the first side segment 14a is positioned between the first sealed channel 9 and a first side seam 15, whereas the second side segment 14b is positioned between the second sealed channel 10 and a second side seam 16. The side seams 15, 16 are configured for joining the upper core cover side 11 to the lower core cover side 12, suitably by means of ultrasonic welding, heat sealing, or the like.

As shown in FIG. 4, the absorbent component 50 is divided into a stiffening segment 13 located between the sealed channels 9,10 and two side segments 14a, 14b on either side of the stiffening segment 13.

Figure 5:
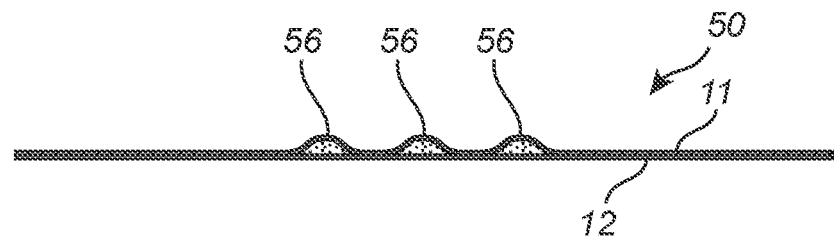
FIG. 5 shows a cross-section taken along the line VI-VI in FIG. 2E.

FIG. 5 shows a cross-section taken through the conformance zone 55 along the line VI-VI in FIG. 2E. Three absorbent clusters 56 are shown in FIG. 5. The absorbent clusters 56 are constituted by accumulations of absorbent material, such as a mixture of pulp fibers and superabsorbent material which are separated by thinner portions of absorbent material. As disclosed herein, the absorbent clusters may alternatively be completely separated by absorbent free channels between the absorbent clusters. The absorbent clusters may have a smaller thickness and a lesser density than the coherent area of the in the crotch portion of the absorbent component. In particular, the absorbent clusters may have a smaller thickness and a lesser density than the oblong high density areas.

With reference to FIG. 2F, the coherent area 51 of the absorbent component 50 is a layer of absorbent material having uniform thickness. The conformance zone 55 is a contiguous conformance zone 55 which is composed of rod-shaped absorbent clusters 56 arranged spaced apart in the transverse direction and in parallel to each other in the longitudinal direction over a triangular area of the absorbent component 50. The rod-shaped absorbent clusters 56 extend in the longitudinal direction from the back edge 53 of the coherent area 51 and form continuations of the coherent area 51. Hence, the back edge 53 of the coherent area 51 constitutes a straight base-line from which the rod-shaped absorbent clusters 56 extend in a direction towards the back end edge (not shown in the figure) of the absorbent article.

Figures 2G, 2H:
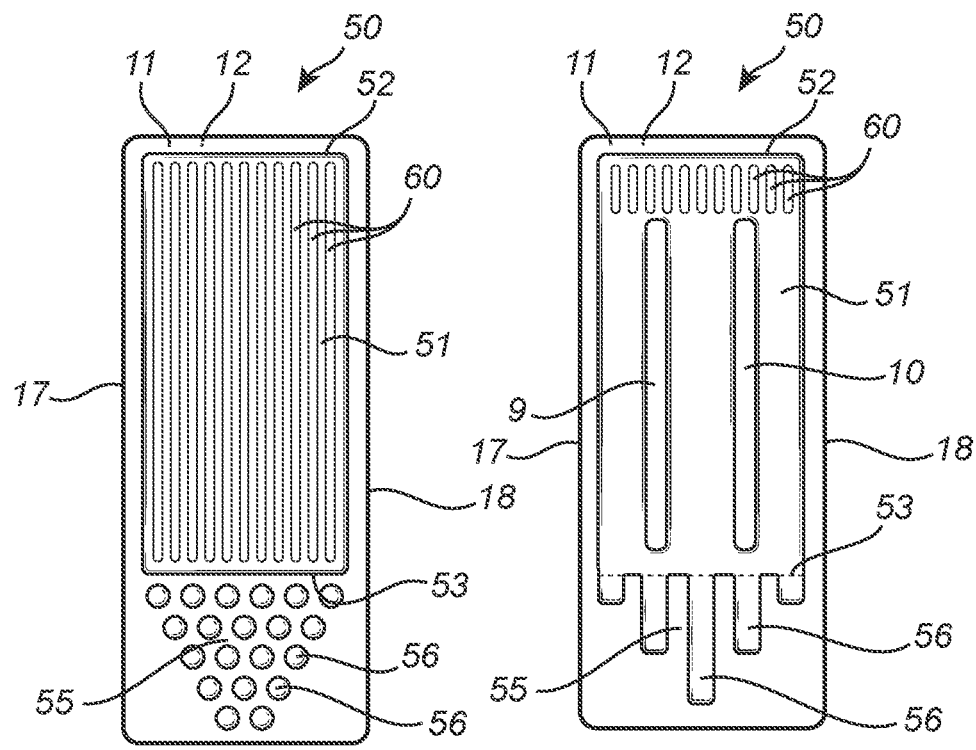

With reference to FIG. 2G, the coherent area 51 of the absorbent component 50 is a layer of absorbent material having oblong high density areas 60 arranged therein. The oblong areas 60 extend generally all the way from the front edge 52 of the coherent area 51 to the back edge 53 of the coherent area 51. The conformance zone 55 is a non-contiguous conformance zone 55 which is composed of circular absorbent clusters 56 arranged in a regular, evenly distributed pattern over a triangular area of the absorbent component 50.

With reference to FIG. 2H, the coherent area 51 of the absorbent component 50 is a layer of absorbent material having oblong high density areas 60 arranged therein. The oblong areas 60 extend in the front portion of the coherent area 51, generally from the front edge 52 of the coherent area 51 to the front ends of two sealed channels 9, 10 which are arranged in the coherent area 51, as disclosed herein. When comparing the absorbent component 50 of FIG. 2H with the absorbent component 50 of FIG. 2E, it can be seen that the oblong areas 60 in FIG. 2H occupy a relatively smaller area of the absorbent component 50 than in the absorbent component 50 shown in FIG. 2E. Instead, the sealed channels 9 10 in FIG. 2H are longer than the sealed channels in FIG. 2E. The sealed channels 9, 10 may optionally be supplemented by side seals as disclosed herein. The conformance zone 55 is a contiguous conformance zone 55 which is composed of rod-shaped absorbent clusters 56 arranged spaced apart in the transverse direction and in parallel to each other in the longitudinal direction over a triangular area of the absorbent component 50. The rod-shaped absorbent clusters 56 extend in the longitudinal direction from the back edge 53 of the coherent area 51 and form continuations of the coherent area 51. Hence, the back edge 53 of the coherent area 51 constitutes a straight base-line from which the rod-shaped absorbent clusters 56 extend in a direction towards the back end edge (not shown in the figure) of the absorbent article.

Figure 2I:
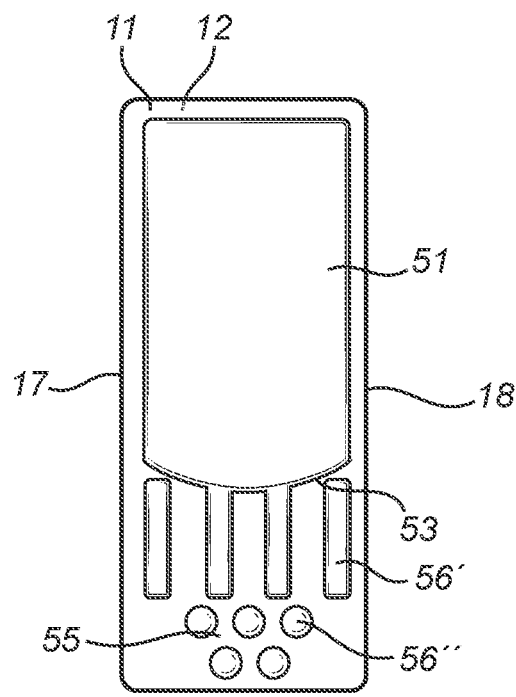

With reference to FIG. 2I, the coherent area 51 of the absorbent component 50 is a layer of absorbent material having uniform thickness. The conformance zone 55 is a contiguous conformance zone 55 which is composed of a set of rod-shaped absorbent clusters 56' arranged spaced apart in the transverse direction and in parallel to each other in the longitudinal direction over a first, rectangular area of the absorbent component 50. Only two centrally arranged rod-shaped absorbent clusters 56' extend in the longitudinal direction from the back edge 53 of the coherent area 51 and form continuations of the coherent area 51. The rod-shaped absorbent clusters 56' on each side of the central rod-shaped absorbent clusters are detached from the coherent area 56. Furthermore, the back edge 53 of the coherent area 51 constitutes a curved base-line from which the two centrally arranged rod-shaped absorbent clusters 56' extend in a direction towards the back end edge (not shown in the figure) of the absorbent article. A second set of absorbent clusters 56", having a circular shape are arranged in a regular, evenly distributed pattern over a generally D-shaped area of the absorbent component 50. The second set of circular absorbent clusters 56" is placed further away from the back edge 53 of the coherent area 51 than the first set of rod-shaped absorbent clusters 56'.

As illustrated by the Figures, the plurality of absorbent clusters 56 in the conformance zone 55 may comprise rod shaped clusters 56, 56', the rod shaped clusters 56, 56' being arranged parallel to each other or generally parallel to each other in the longitudinal direction of the absorbent article 1. The rod-shaped clusters 56 may be distributed in the transverse direction over a triangular area of the absorbent core 5, the triangular area having its base arranged at the back edge 53 of the coherent area 51 and its tip arranged on the central longitudinal axis y1 of the absorbent article and facing the back end edge of the absorbent article 1.

The back edge 53 of the coherent area 51 may be non-linear, as shown in FIGS. 2E and 2I.

As disclosed herein, the absorbent article 1 may be provided with components such as elastic barrier cuffs, elastic side panels, skin care agents, odour control material and other components which are commonly used in absorbent articles such as for example baby diapers or incontinence garments. Such additional components are well known in the art and are not described in further detail here.

The disclosure may be varied within the disclosed scope. For example, the materials and dimensions used for the different layers forming the absorbent article 1 may be varied, as indicated above. The absorbent article may further include standing gathers, side panels, fastening systems, etc., as known sealed channels 9, 10 in the art and depending of the type of absorbent article intended.

The invention claimed is:

1. An absorbent article comprising an absorbent core sandwiched between a liquid-permeable topsheet and a liquid-impermeable backsheet, said article having a longitudinal direction along a central longitudinal axis (y1) and a transverse direction along a central transverse axis (x1) extending perpendicular to said longitudinal axis (y1), said absorbent article having a front end edge and a back end edge extending in said transverse direction and a first side edge and a second side edge extending in said longitudinal direction, said absorbent article comprising a front portion, a back portion and a crotch portion located between said front portion and said back portion, wherein said absorbent core comprises an absorbent component, said absorbent component being enclosed by a core cover comprising an upper side and a lower side, said absorbent component comprising a coherent area, said coherent area having an extension in said longitudinal direction in at least said front portion and said crotch portion of said absorbent article and having an extension in said transverse direction over a full width of said absorbent component inside said core cover, said coherent area having a front edge and a back edge, wherein said back portion of said absorbent article further comprises a conformance zone, said conformance zone comprising 2 to 200 absorbent clusters, wherein the absorbent clusters have indistinct peripheral edges and are fully or partly interconnected by thinned edge portions of the clusters.

2. Absorbent article according to claim 1, wherein said coherent area comprises absorbent cellulose fibres.

3. Absorbent article according to claim 1, wherein said absorbent clusters in said conformance zone have a circular, oval or polygonal shape.

4. Absorbent article according to claim 1, wherein said absorbent clusters are clusters comprising or consisting of absorbent cellulose fibres.

5. Absorbent article according to claim 1, wherein said conformance zone comprising said plurality of absorbent clusters is non-contiguous with said coherent area of said absorbent core.

6. Absorbent article according to claim 1, wherein said conformance zone comprising said plurality of absorbent clusters is contiguous with said coherent area, at least one of said absorbent clusters extending continuously in said longitudinal direction from said back edge of said coherent area.

7. Absorbent article according to claim 1, wherein said absorbent clusters in said plurality of absorbent clusters are evenly distributed in said transverse and/or in said longitudinal direction in said back portion of said absorbent article.

8. Absorbent article according to claim 1, wherein said conformance zone is symmetrically orientated in relation to said longitudinal axis and wherein said conformance zone has a triangular shape, a D shape, a W shape or a rectangular shape.

9. Absorbent article according to claim 1, wherein a number of absorbent clusters in said transverse direction of said conformance zone decreases in a direction towards said back end edge of said absorbent article.

10. Absorbent article according to claim 1, wherein said absorbent clusters are circular absorbent clusters having a diameter of from 2 to 45 mm.

11. Absorbent article according to claim 1, wherein said plurality of absorbent clusters in said conformance zone comprises rod shaped clusters, said rod shaped clusters being arranged parallel to each other or generally parallel to each other in said longitudinal direction of said absorbent article and being distributed in said transverse direction over a triangular area of said absorbent core, said triangular area having its base arranged at said back edge of said coherent area and its tip arranged on said central longitudinal axis (y1) of said absorbent article and facing said back end edge of said absorbent article.

12. Absorbent article according to claim 1, wherein said back edge of said coherent area is non-linear.

13. Absorbent article according to claim 1, wherein said coherent area of said absorbent core comprises oblong high density areas of absorbent material extending in said longitudinal direction at least in a front portion of said coherent area.

14. Absorbent article according to claim 13, wherein said oblong areas extend in said longitudinal direction substantially from said front edge to said back edge of said coherent area.

15. Absorbent article according to claim 13, wherein a density of absorbent material is higher in said oblong areas than in said plurality of absorbent clusters in said conformance zone in said back portion of said absorbent article.

16. Absorbent article according to claim 1, wherein an absorbent material composition is the same in said coherent area and in said conformance zone.

17. Absorbent article according to claim 1, wherein said absorbent component comprises a sealing arrangement for joining said upper and lower sides of said core cover.

18. Absorbent article according to claim 1, wherein said absorbent component comprises two sealed channels extending in said longitudinal direction in said crotch portion, said sealed channels being free or substantially free from absorbent material and having seals extending therein, said seals joining said upper and lower sides of said core cover within said sealed channels.

19. Absorbent article according to claim 18, comprising two side seams being arranged along longitudinal side edges of said absorbent component, wherein a stiffening segment is defined in said absorbent component between said sealed channels, and two side segments are defined in said absorbent component outside each sealed channel between each said sealed channel and a corresponding one of said side seams.

20. Absorbent article according to claim 1, wherein the absorbent article is a wearable and disposable absorbent article selected from open diapers, pant diapers, belted diapers, incontinence garments, feminine hygiene garments, and absorbent inserts which are worn inside a support garment.

\* \* \* \* \*